United States Patent
Stern et al.

[11] Patent Number: 6,031,225
[45] Date of Patent: Feb. 29, 2000

[54] SYSTEM AND METHOD FOR SELECTIVE SCANNING OF AN OBJECT OR PATTERN INCLUDING SCAN CORRECTION

[75] Inventors: Howard Stern, Greenlawn; Kuo-Ching Liu, New York; Robert C. Blosser, Northport, all of N.Y.

[73] Assignee: Robotic Vision Systems, Inc., Hauppauge, N.Y.

[21] Appl. No.: 09/019,479

[22] Filed: Feb. 5, 1998

[51] Int. Cl.[7] .......................... G02B 26/10; G01B 11/00; G01N 21/00
[52] U.S. Cl. .................. 250/235; 250/234; 250/559.34; 250/559.4; 250/559.06; 356/376; 359/202
[58] Field of Search ...................... 250/235, 234, 250/236, 559.34, 559.4, 559.04, 559.29, 559.48, 559.49, 559.06; 356/376, 375; 359/202, 201, 197; 348/90, 92, 93; 358/486, 494, 496, 497

[56] References Cited

U.S. PATENT DOCUMENTS

| | | | |
|---|---|---|---|
| 4,788,423 | 11/1988 | Cline | 250/235 |
| 4,957,369 | 9/1990 | Antonsson | 356/376 |
| 5,463,227 | 10/1995 | Stern et al. | 250/559.29 |
| 5,663,825 | 9/1997 | Amon et al. | 359/207 |
| 5,712,678 | 1/1998 | Hofmann | 348/117 |

*Primary Examiner*—John R. Lee
*Attorney, Agent, or Firm*—Kenyon & Kenyon

[57] ABSTRACT

A system and method for correcting a scan pattern of a moving optical scanning system. A gantry moves an optical system at a constant rate in a first direction. Using a light source and a first deflector, the optical scanning system quickly sweeps a light beam in a direction orthogonal to the motion of the gantry by changing the angle of deflection of the first deflector linearly with time. To compensate for the motion of the gantry, the optical system includes a second deflector which deflects the light, the deflection angle being determined as a function of the velocity of the gantry. The deflected light is focussed on the object (or pattern). Accordingly, the object is scanned along a corrected scan line orthogonal to the X-axis. The optical scanning system may optionally perform "selected" scanning. Also, the optical system optionally employs a "look-ahead/look-behind" scanning approach to further improve the rate at which portions of an object (or pattern) may be inspected.

52 Claims, 11 Drawing Sheets

SYSTEM AND METHOD FOR SELECTIVE SCANNING OF AN OBJECT OR PATTERN INCLUDING SCAN CORRECTION

FIELD OF INVENTION

The present invention is directed to a system and method for scanning an object or pattern.

BACKGROUND OF THE INVENTION

Machine vision systems are commonly used in industry for high speed inspections. In particular, these systems are used to obtain digital images of objects in order to determine, with a computer, whether the object is of "acceptable" quality with respect to predetermined specifications. For example, a system may inspect a semiconductor chip package to determine whether each of the leads of the package has the proper dimension. A system may also inspect for coplanarity of solder balls on ball grid arrays.

Patterns such as bar codes and data codes are also imaged by such systems. Images of these patterns are analyzed by a computer in order to "read" the information represented by these codes.

In a machine vision system, an object (or pattern) is typically imaged by scanning the object with a light source and capturing the light reflected from the object with a video camera (i.e., a photodetector). A digital image is formed from the image received by the camera and the digital data is analyzed by a computer in order to determine characteristics of the object or pattern.

FIG. 1 illustrates a scan pattern of a typical machine vision system scanning an object (e.g., ball grid array 130). A gantry (not shown) supporting an optical system (including a laser light source) moves at a constant rate along (or parallel to) the X-axis. A laser beam is swept at a constant rate (using, for example, a single acousto-optic deflector) in a direction parallel to the Y-axis (and orthogonal to the X-axis). As a result, the scan lines (a–b and c–d) are parallel to each other. However, the scan lines are not orthogonal to the X-axis due to the motion of the gantry. Accordingly, portions of object features are not scanned adequately. As shown in FIG. 1, for example, while the left portion of object feature 101 is scanned, the corresponding portion of object feature 102 is not scanned. Accordingly, data related to the object feature 102 may be incomplete.

Moreover, in the system illustrated in FIG. 1, each spot of reflected light is collected from each point along the entire length of each scan line. Data points related to the light reflected from each point are processed and stored. Data points which include no information about the object features (such as along scan line e–f) are also collected.

SUMMARY OF THE INVENTION

The present invention provides a system and method for correcting a scan pattern of a moving optical scanning system. In an exemplary embodiment, the optical scanning system is mounted on a gantry, and positioned above an object (or pattern) to be scanned. The gantry includes a motion mechanism for positioning the optical system to different X-Y positions above the object (or pattern). The gantry moves the optical system at a constant rate along (or parallel) to an X-axis. Using a light source and a first deflector, the optical scanning system quickly sweeps a light beam in a direction orthogonal to the motion of the gantry by changing the angle of deflection of the first deflector linearly with time. To compensate for the motion of the gantry, the optical system of the exemplary embodiment includes a second deflector which deflects the light (deflected by the first deflector) in a direction opposite the motion of the gantry thereby compensating for the motion of the gantry, the deflection angle being determined as a function of the velocity of the gantry. The deflected light is focussed on the object (or pattern). Accordingly, the object is scanned along a corrected scan line orthogonal to the X-axis.

The optical scanning system of the present invention may also optionally perform "selected" scanning. In particular, the optical scanning system directs light to various portions of an object along scan lines. Data points related to the light reflected from only selected portions of the object, rather than the entire object, are collected. Accordingly, the amount of data analyzed and stored is reduced thereby conserving resources. Additionally, the scanning velocity may be increased since there is less total data collected and processed.

In another embodiment, the optical system optionally employs a novel "look-ahead/look-behind" scanning approach to further improve the rate at which portions of an object (or pattern) may be inspected.

DETAILED DESCRIPTION

Scan Correction

Figure 2:
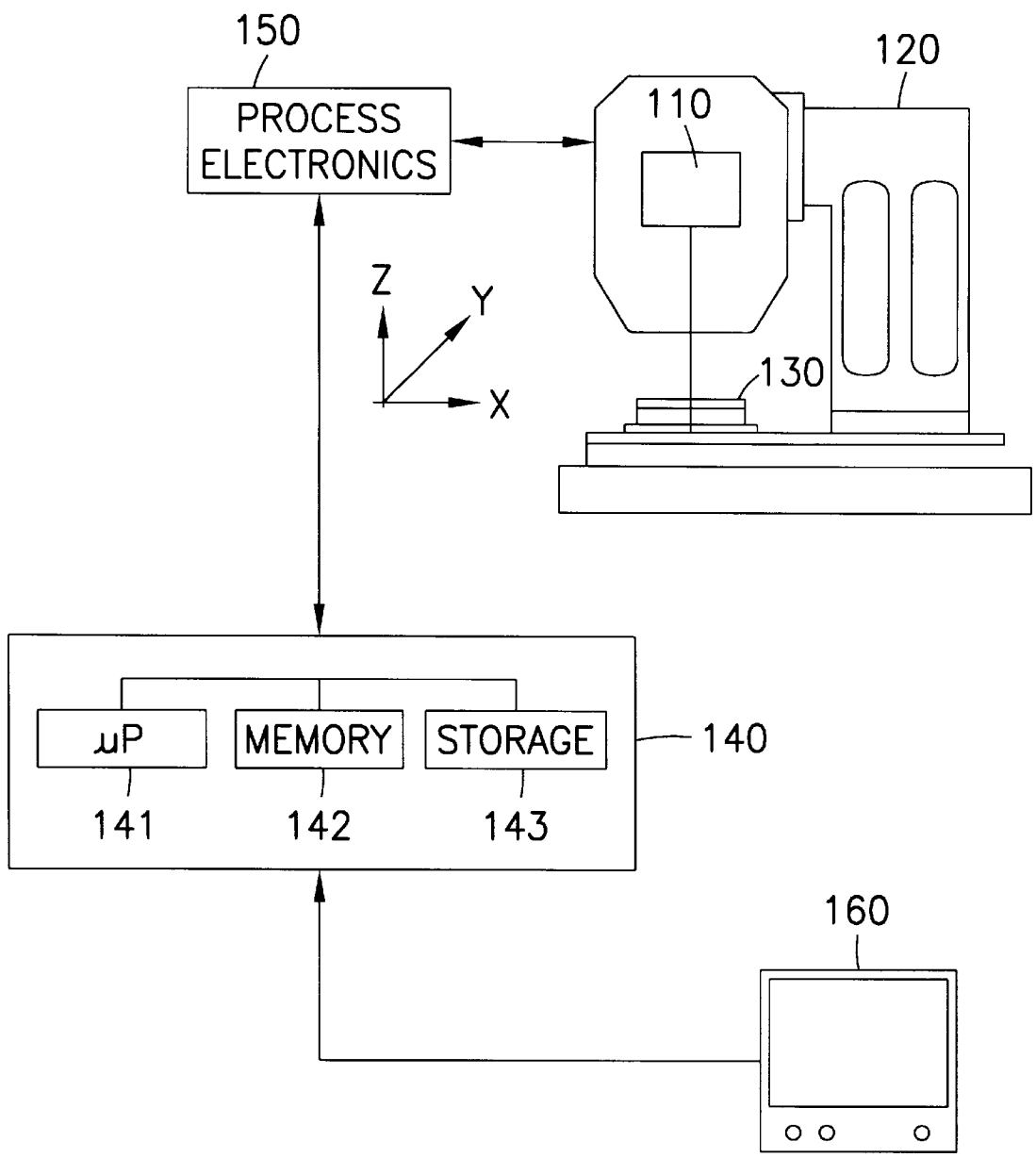
FIG. 2 is a diagram of the overall system architecture of one embodiment of the present invention.

Referring to FIG. 2 of the drawings, there is illustrated the overall system architecture of one embodiment of the present invention. An optical system 110 is mounted on, for example a gantry 120 (or, e.g., another X-Y motion mechanism), and positioned above an object (or pattern) to be scanned (or imaged) such as a ball grid array (BGA) 130. The gantry 120 includes a motion mechanism (not shown) such as that described in U.S. Pat. No. 5,463,227 issued to Stern et al., expressly incorporated herein by reference, for positioning the optical system 110 to different X-Y positions above the BGA 130. The motion mechanism may be controlled by a computer 140 (which includes, for example, a microprocessor 141, a memory device 142, and a program storage device 143) to maintain a predetermined speed during scanning. The instantaneous position of the scanning axis is transmitted by axis encoders mounted to the gantry 120 to the process electronics 150 and hence to the computer 140.

In an alternative embodiment, the object (here, BGA 130) may instead be moved by a motion mechanism, and the position of the optical system 110 may remain constant. Or, both the object and the optical system 110 may be moved, relative to one another.

Data collected by the optical system 110 is transmitted as an analog signal to the process electronics 150. The process electronics 150, which includes, for example, digital signal processors (DSPs), digital to analog (D/A) converters, analog to digital (D/A) converters, and input/output (I/O) and connection links, receives and processes the analog data. The processed data is transmitted to the computer 140 for analysis. The results of the analysis are reported to the operator on output device 160.

Figure 3A:
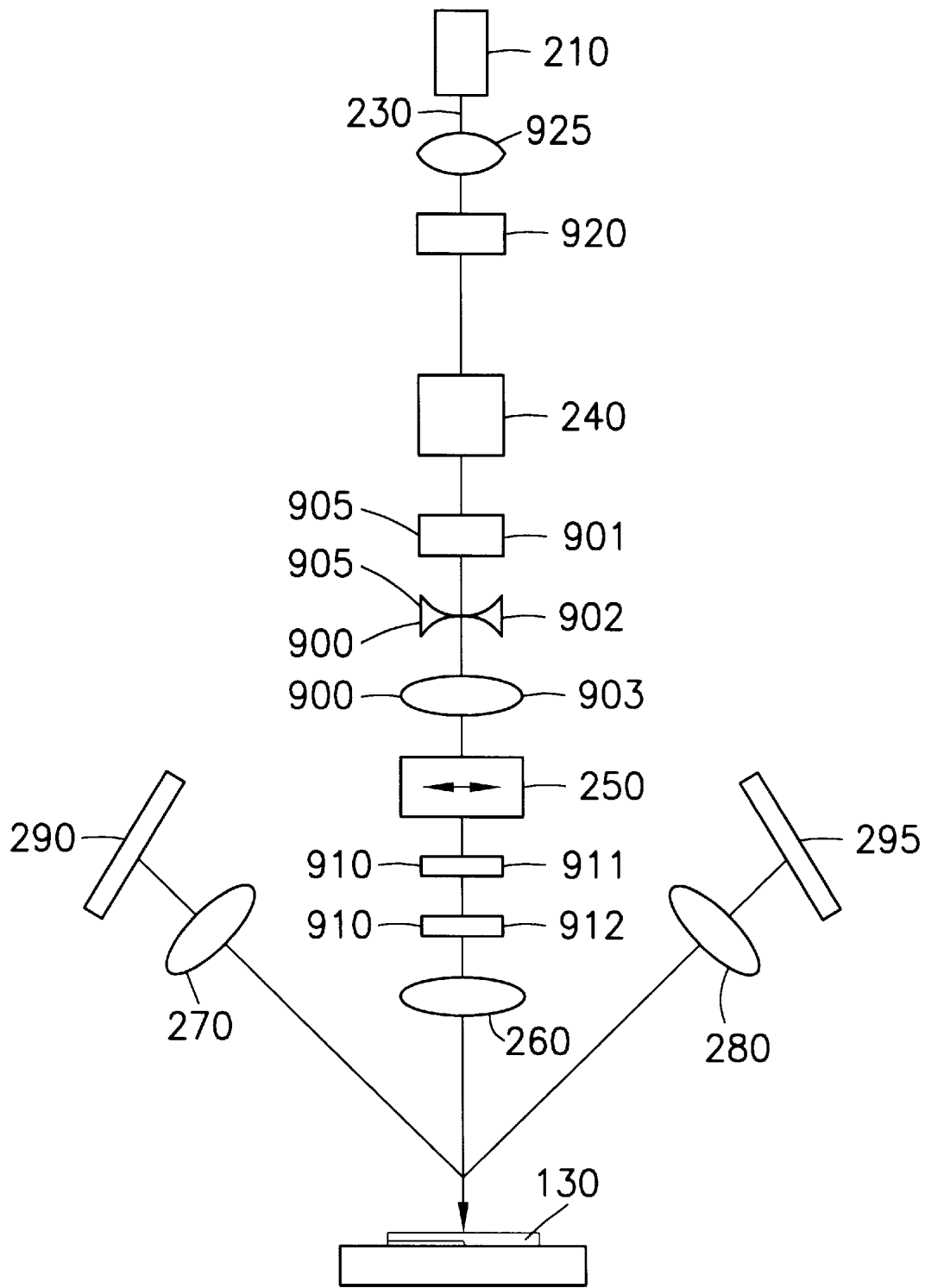
FIG. 3A illustrates the front plan view of the optical system of FIG. 2.
Figure 3B:
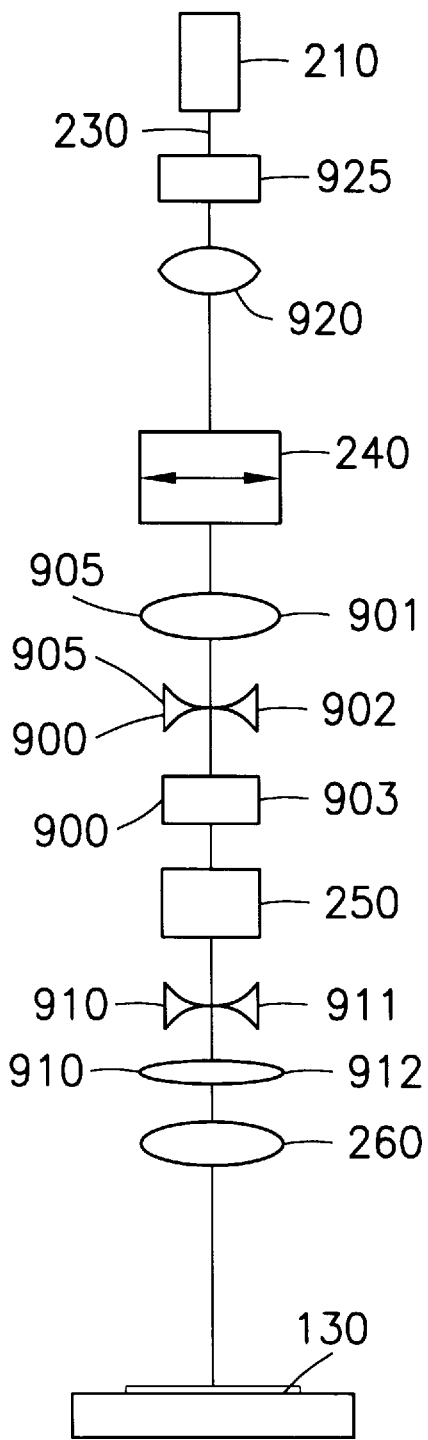
FIG. 3B illustrates the side plan view of the optical system of FIG. 2.

FIGS. 3A and 3B illustrate the front plan view and side plan view (respectively) of the optical system 110 of the system of FIG. 2. A light source 210 (for example, a laser diode) controlled by process electronics 150, is positioned by gantry 120 to illuminate an object such as a BGA 130. Light, for example, a laser beam 230 is directed to a first deflector 240 through cylindrical collimators 925 and 920. In the exemplary embodiment, collimators 925 and 920 provide the proper beam shape for the first deflector 240, e.g., wide in the scan (or deflection) direction and narrow in the traverse direction. This provides collimation and spot resolution in the scan direction and minimizes the aperture needed by the first deflector 240 traverse to the scan direction.

The first deflector 240 selectively deflects the laser beam 230. In particular, the first deflector 240, controlled by process electronics 150, includes, for example, an acousto-optic (A.O.) deflector (although another deflection device such as a mirror galvanometer could be used as an alternative). The laser beam 230 is quickly and continuously "swept" in a scan line across a predetermined area of the BGA 130, in a direction (along or parallel to a Y-axis) orthogonal to the gantry motion (i.e., along or parallel to an X-axis) by linearly (with time) changing the drive frequency to the deflector 240 and thereby linearly (with time) changing the deflection angle of the laser beam 230.

From the first deflector, the laser beam 230 is directed to a second deflector 250 through, for example, a beam compressor 905 (comprised of lenses 901 and 902) and a beam expander 900 (comprised of lenses 902 and 903). (In this embodiment, the beam compressor 905 and beam expander 900 share lens 902.) Beam compressor 905 and beam expander 900 are, in this embodiment, cylindrical telescopes which optimize the beam shape output by the first deflector 240 for the second deflector 250. Here, the beam compressor 905 and beam expander 900 narrow the beam where it is wide and widen the beam where it is narrow.

In the exemplary embodiment, the second deflector 250, controlled by process electronics 150, includes, for example, an A.O. deflector (although another type of deflector such as a mirror galvanometer could be used). This second deflector 250 performs scan "correction" by increasingly deflecting the laser beam 230 (i.e., linearly changing the deflection angle) along (or parallel to) the X-axis at a rate proportional to the rate of travel of the gantry along (or parallel to) the X-axis.

The laser beam deflected by the second deflector 250 is directed to a beam expander 910 (a cylindrical telescope comprised of lenses 911 and 912) which alters the shape of the beam so that the beam has the same diameter in the X and Y directions.

Finally, an optical system 260 comprised of, for example, spherical scan lenses, focusses the laser beam to a spot on the surface of the BGA 130 (or other object or pattern being imaged).

Light impinging the BGA 130 and reflected therefrom is focussed through optical focussing systems 270, 280 (comprised of, for example, spherical elements) onto photo sensitive devices 290, 295 (position sensitive or sensing devices, photo sensitive diodes, diode arrays, etc.) (optical focussing systems 270, 280 and photo sensitive devices 290, 295 are illustrated in only one view, i.e., FIG. 3A). The BGA 130 imaging optics (i.e., optical focussing systems) 270, 280 and photo sensitive devices 290, 295 may be arranged, for example, as shown to satisfy the well known Scheimpflug condition to focus along the plane of the object (here, BGA 130).

Analog signals generated by the photo sensitive devices 290, 295 are transmitted to the process electronics 150 and are processed and analyzed by process electronics 150 and computer 140. Information collected by the photo sensitive devices 290, 295 may be used, for example, to determine Z coordinates of points on BGA 130 using standard optical triangulation techniques, as described in U.S. Pat. No. 4,957,369 to Antonsson, expressly incorporated herein by reference.

Information from the photosensitive devices 290, 295 may also be used by the process electronics to module the laser intensity or the time that the laser beam is active at each of the scanned points to strengthen or reduce the beam energy delivered to that point in accordance with the received energy being too small or too large, respectively, due to the targets reflectance or specularity characteristics.

In the exemplary embodiment, the laser beam image is spatially quantized so that a number of discrete image points are formed along the scan line rather than a continuous image line. This may be accomplished by, for example, pulsing or shuttering the laser 210. Alternatively a continuous (CS) laser could be used and the imaging device may be operated in a sampling mode to obtain the quantization.

In operation, the gantry 120 (and accordingly the optical system 110) moves at a constant rate along (or parallel to) an X-axis. As noted above, the first deflector 240 causes the laser beam 230 to scan the BGA 130 in a direction (along or parallel to a Y-axis) orthogonal to the gantry 120 motion by linearly changing, with time, the drive frequency to the first deflector 240 For a deflector 240 such as an A.O. deflector, the amount of deflection is controlled by the application of a control voltage to the drive electronics of the deflector 240. The control voltage input is converted by the drive electronics into a varying frequency output signal in a voltage controlled oscillator (vco) section with the frequency being directly proportional to the amplitude of the input voltage.

The A.O. deflector deflects the illumination beam by an amount which is proportional to the frequency. In the exemplary embodiment, after the maximum Y position is reached, the deflection along (or parallel to) the Y axis is reset (in a short time compared to scan time) to deflect the beam to the minimum Y position and the next scan line is initiated. The laser beam may be turned off during reset. Of course, as an alternative, the beam deflection may be reversed to create a triangular rather than sawtooth scan pattern.

Figure 4:
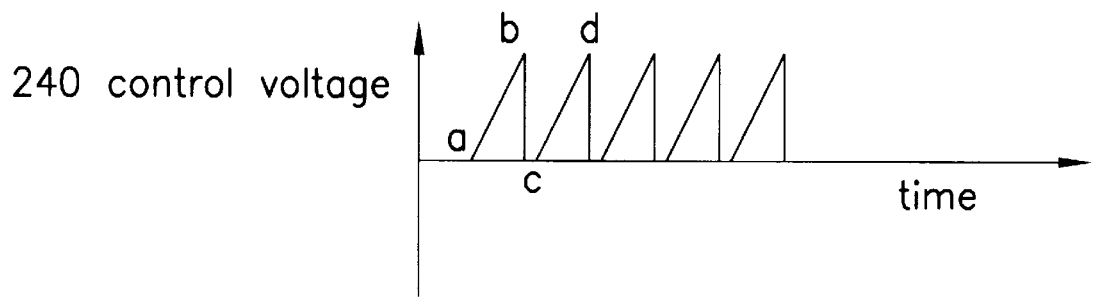
FIG. 4 illustrates an exemplary scan control voltage wave form associated with the first deflector of FIGS. 3A and 3B.

FIG. 4 illustrates an exemplary scan control voltage wave form associated with the first deflector (for five scan lines). As illustrated, the first scan line begins (a) and voltage increases linearly for time t when the laser beam reaches its maximum Y position (b). The deflector is reset (b–c) and the second scan line begins (c).

Figure 5:
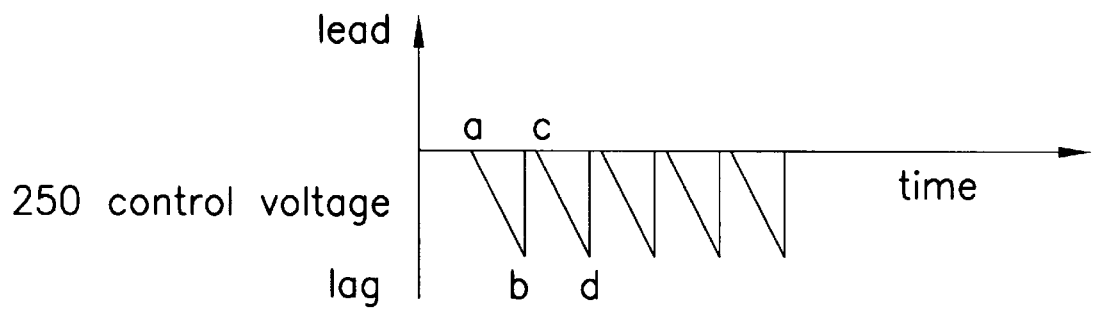
FIG. 5 illustrates an exemplary scan control voltage wave form associated with the second deflector of FIGS. 3A and 3B.

In addition to the Y-axis deflection by the first deflector 240, the second deflector 250 deflects the laser beam along (or parallel to) the X-axis and, in this embodiment, in the opposite direction of the gantry motion in order to compensate for the changing gantry position (over time at a constant rate). For each scan line, a linearly changing drive frequency is applied to the second deflector 250. FIG. 5 illustrates an exemplary scan control voltage waveform associated with the second deflector 250 (for five scan lines). As illustrated, the first scan line begins (a) and voltage decreases linearly (increasing scan lag) for time t (when the laser beam reaches its maximum Y position (b)). The deflector is reset (b–c) and the second scan line begins (c). The effect of the correction deflection is to othogonalize the scan.

Figure 6:
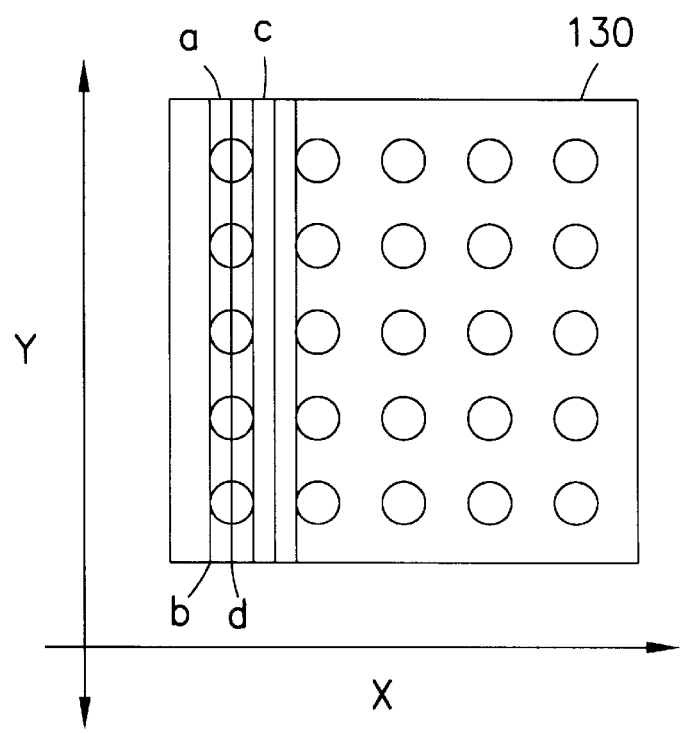
FIG. 6 illustrates the scan lines on a BGA as a result of the performance of the exemplary corrected scanning.

FIG. 6 illustrates the scan lines on the BGA 130 as a result of the performance of the above-described corrected scanning. As shown, the scan lines a–b, c–d, etc. are generally parallel to each other and to the Y axis. In accordances with FIGS. 4, 5, and 6, the gantry 120 moves the optical system by a distance (c–d) or (d–b) from a position orthogonal to scan line a–b to a position orthogonal to scan line c–s, in a time t+τ where t is the time it takes the first deflector 240 to sweep the laser beam once across the area of interest and τ is the time it takes the first deflector 240 to reset to begin a second scan line. Here, the scan lines will be spaced at a distance d where $$s = v^*(t+\tau)$$

(v=velocity of the gantry).

Note that since, for each particular illuminated spot on an object, the X and Y coordinates will be known based on the position of the gantry and the angles at which the deflectors 240, 250 deflect the source laser beam, the Z coordinate of each point may be easily calculated using standard optical triangulation techniques.

In a second illustrative embodiment, the second deflector 250 deflects the laser beam along (or parallel to) the X-axis embodiment in the same direction as the gantry motion (i.e., to positions ahead of the optical system) in order to compensate for the changing gantry position (over time at a constant rate). For each scan line, a linearly changing drive frequency is applied to the second deflector 250. The x-axis "lead" is decreased with time to orthogonalize the scan.

Figure 7:
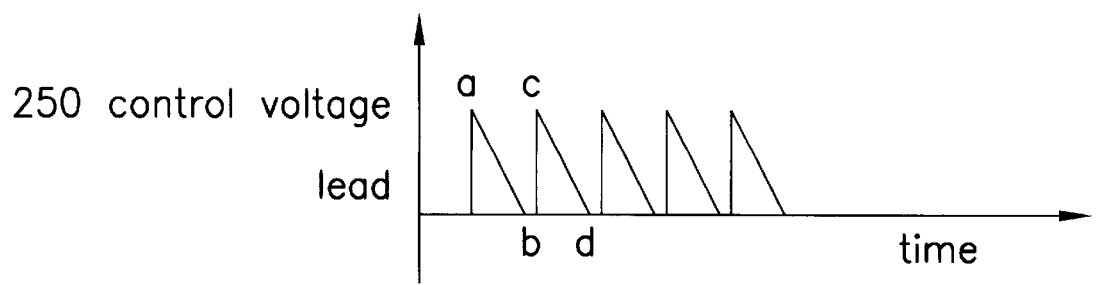
FIG. 7 illustrates an exemplary scan control voltage wave form associated with the second deflector in a second illustrative embodiment of the present invention.

FIG. 7 illustrates an exemplary scan control voltage wave form associated with the second deflector 250 (for five scan lines) in the second illustrative embodiment of the present invention. As illustrated, the first scan line begins (a) and voltage decreases linearly for time t (when the laser beam reaches its maximum Y position (b)). The deflector is reset (b–c) and the second scan line begins (c).

While exemplary embodiments have been illustrated and described, it will be understood by those skilled in the art that various changes in form and details may be made therein without departing from the spirit and scope of the invention. For example, in the above described embodiments, two deflectors (i.e., deflectors 240 and 250) are utilized, the first deflector deflecting light along (or parallel to) a Y-axis (with the deflection angle changing linearly with time), the second deflector deflecting the light deflected by the first deflector along (or parallel to) an X-axis (with the deflection angle changing linearly with time). It is possible for the first deflector to instead deflect along or parallel to the X-axis while the second deflector deflects the light deflected by the first deflector along or parallel to the Y-axis. Additionally, it may be possible to instead utilize a single deflection device (instead of the two deflectors) capable of changing deflection angles in both directions (i.e., capable of scanning in both the X direction and Y direction, or in two dimensions), such as, for example, a mirror having two axes of rotation wherein the axes of rotation are orthogonal to one another.

Selected Scanning

The optical scanning system 110 of the present invention may also optionally perform "selected" scanning. In particular, the optical scanning system 110 directs light to various portions of an object, for example, along scan lines. Data points related to the light reflected from only selected portions of the object, rather than the entire object, are collected. Accordingly, the amount of data analyzed and stored is reduced thereby conserving resources. Additionally, the scanning velocity may be increased since there is less total data collected and processed.

In accordance with the exemplary embodiment, process electronics 150 under the control of the computer 140 collects data points (via photo sensitive devices 190, 195) only along scan lines intersecting object features of interest. In the example shown in FIG. 8, data points 820 along scan lines 810 intersecting solder balls 840 on BGA 130 are collected.

The computer 140 controls the process electronics 150 to collect data points 820 (via photo sensitive devices 190, 195) only along scan lines that intersect a solder ball 840 in accordance with a stored program. The stored program (stored in, for example, storage device 143) includes information concerning the geometry of the BGA 830. For example, the stored program may include information derived from a BGA specification, or derived from an earlier obtained image of a sample BGA. Accordingly, the scanning system of the present invention has a priori knowledge of where each of the solder balls 840 should be positioned on BGA 130.

Figure 8:
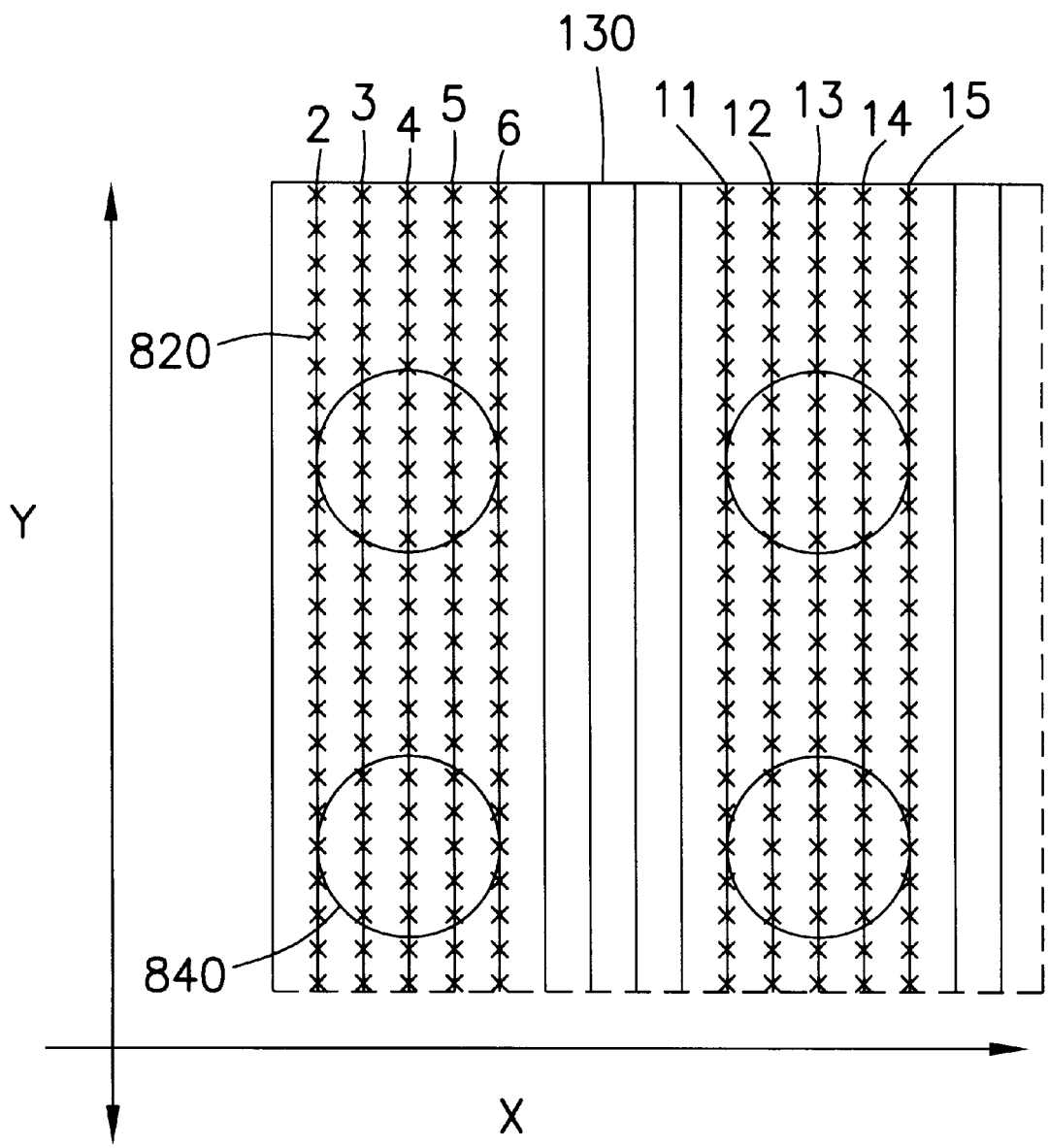
FIG. 8 illustrates the selective collection of data points in one embodiment of the present invention.

In FIG. 8, it is expected that the features of interest, here the solder balls 840, will only be positioned along scan lines 2–6 and 11–15. Accordingly, the process electronics 150 is controlled only to collect data along scan lines 2–6 and 11–15, i.e., all data points at predetermined X coordinates. The X-Y coordinate of each point is known by the system since it is a function of the position of the gantry 120 (and, in particular, the optical system 110) and the angles that the deflectors 240, 250 deflect the laser beam 230.

In this embodiment, the first deflector 240 directs or sweeps (or pulses) the laser beam 230 across the BGA 130 along each of the lines 1–17, even though data is only collected along a subset of these lines. In an alternative embodiment, the process electronic 150 may optionally turn off (or pause) the light source 210, and/or deflectors 240, 250 while the gantry 120 moves the optical system 110 between lines 6 and 11. The velocity of the gantry 120 may also be increased between these lines (6–11) since no data is simultaneously collected.

Figure 1:
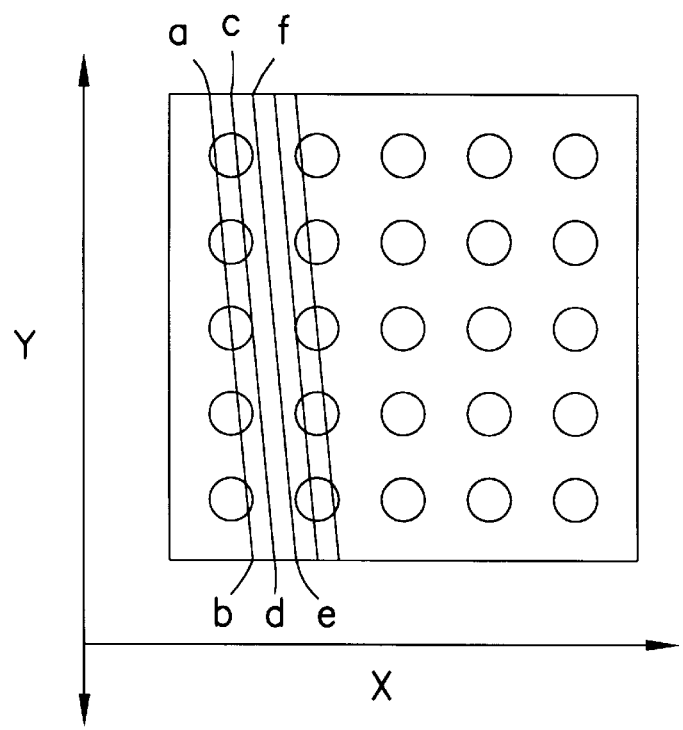
FIG. 1 illustrates a prior art scan pattern.

The scan lines 1–17 illustrated in FIG. 8 have been corrected using the second deflector 250 and correction techniques as described above. However, it is possible to selectively scan in accordance with this invention without the correction. Uncorrected, the resulting scan lines would appear similar to those shown in FIG. 1.

Figure 9:
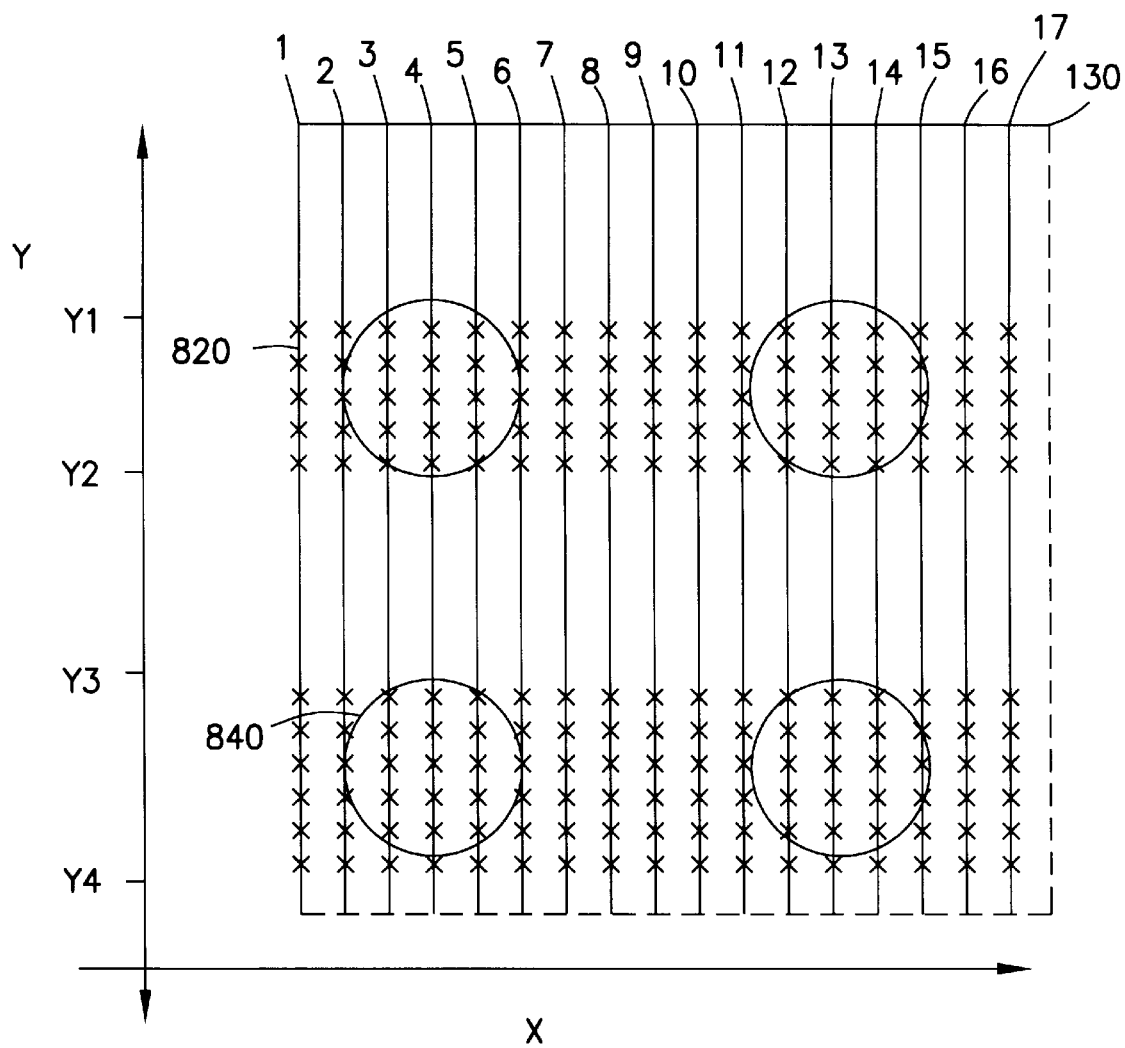
FIG. 9 illustrates the selective collection of data points in another embodiment of the present invention.

FIG. 9 illustrates a variation of the present invention. In this embodiment, the computer 140 and process electronics (via photo sensitive devices 190, 195) selectively collect data points 910 along each line 1–17 only at particular Y coordinates where it is expected that object features of interest, such as solder balls 840, will be present (in accordance with, for example, a BGA specification). Here, the first deflector 240 directs the laser beam 230 along each line 1–17, but data is not collected or analyzed for light reflected from the surface of the BGA 130 at locations other than those at predetermined Y coordinates (here, Y1–Y2 and Y3–Y4).

In the embodiment of FIG. 9, the deflection angle of the deflector 240 changes linearly (and, at a constant rate) with time as described in connection with FIG. 4 under the control of the process electronics 150. As an alternative, the deflection angle of the first deflector 240 may change at one rate while data is collected by computer 140 and process electronics 150 (e.g., for Y1–Y2 and Y3–Y4), and may change at a second, faster rate during the time that data is not collected (i.e., for Y2–Y3). The deflection angle may be also change at one rate while data is collected (e.g., for Y1–Y2) and then may be changed almost instantaneously so that the beam skips the portion of the object from which data is not being collected (e.g., Y2–Y3), and begins scanning again at the next data collection point (e.g., Y3). Also, the light source 210 may optionally be turned off (or paused) while the deflection angle is changing at the faster rate (or is changed to skip a portion of the object) since data is not being collected. As before, the gantry velocity is set to move the gantry by the distance between scan lines during the total of the scanning time and the reset time.

Accordingly, not only are valuable resources conserved, but also the speed at which the information of interest is gathered and analyzed is increased. In the illustrative embodiment, the information of interest is the information received as a result of impinging light on the solder balls 840, for example, in order to determine Z coordinates using standard optical triangulation techniques.

Figure 10:
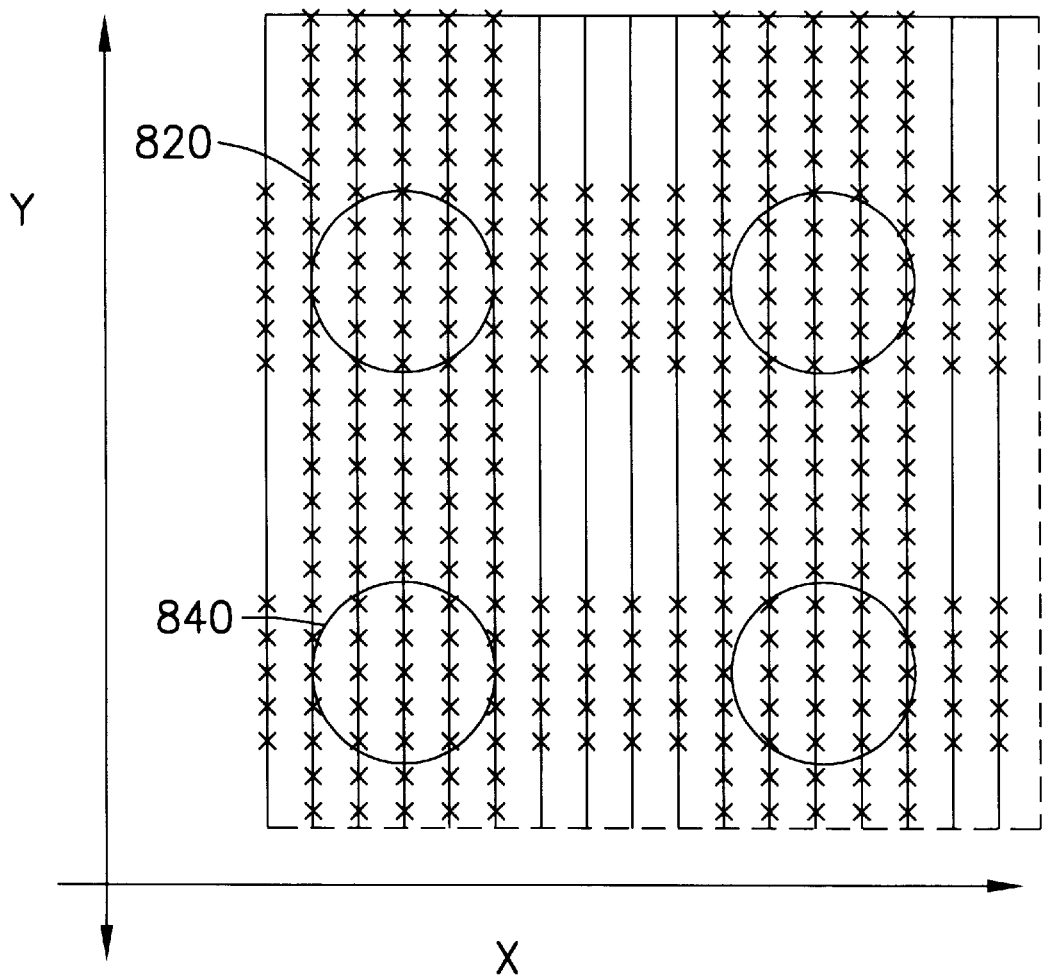
FIG. 10 illustrates the selective collection of data points in an additional embodiment of the present invention.

In another embodiment of the present invention, the method described in connection with FIGS. 8 and 9 may be combined in order to obtain data points 820 as illustrated in FIG. 10.

Look-Ahead/Look-Behind Scanning

Deflectors 240, 250 (A.O., rotating polygons, mirror galvanometers and the like), as well as pulsed laser sources (light source 210) can be operated at very high speeds. However, the rate at which photo sensitive devices (190, 195) can collect data (sense reflected light), may be somewhat of a limiting factor in terms of possible overall system performance gains that would be otherwise achievable in accordance with the selected scanning described above. Also, since the gantry 120 is mechanical, it cannot move instantaneously between two points. Thus, if the velocity of the gantry 120 is set to allow time for the photo sensitive devices 190, 195 to collect data along a scan line intersecting a feature of interest, it cannot move instantaneously to a position orthogonal to the next feature of interest.

Specifically, in connection with FIGS. 8 and 10, one would like to move the gantry 120 instantaneously from a position orthogonal to a scan line intersecting the end of one ball (scan line 6) to the beginning of the next ball (scan line 11) since no data is collected between the balls. Mechanical devices, however, cannot move instantaneously.

In one exemplary embodiment of the present invention, the optical system 110 optionally employs a novel "look-ahead/look-behind" scanning approach to further improve the rate at which portions of an object may be inspected. Such an approach is particularly useful when collecting data points 820 as described in connection with FIGS. 8 and 10. That is, "look-ahead/look-behind" scanning is particularly well suited for use in a system where it is desired to increase the velocity of a gantry 120 relative to the velocity at which photosensitive devices 190, 195 (and corresponding process electronics 140 and computer 150) can collect data for one scan line.

According to the exemplary embodiment, a stepped control voltage waveform (as a function of time) is applied to a deflector (here, A.O. deflector 250) in order to deflect a source laser beam 230 selectively to positions ahead of or behind a current gantry position (with respect to the motion of the gantry 120 along the X axis). This operates in a similar fashion as the scan correction discussed above.

Figure 11:
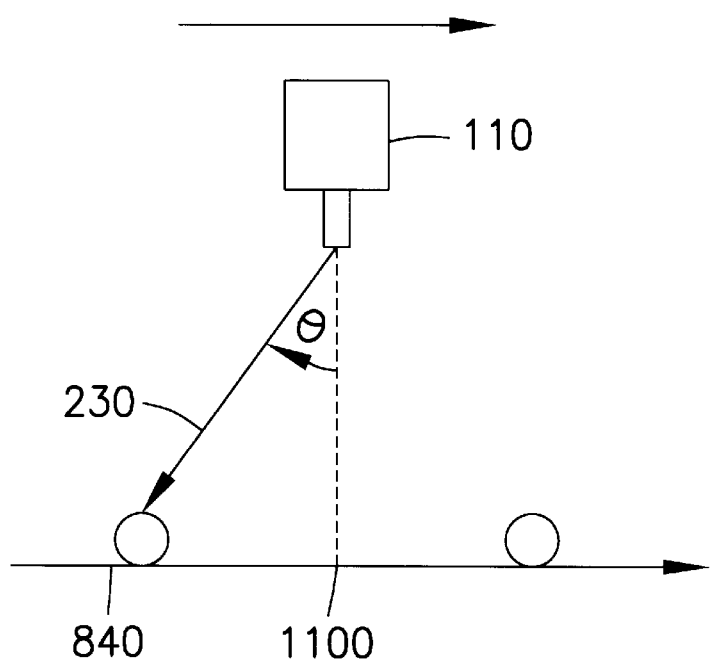
FIG. 11 illustrates "look-behind" scanning of the exemplary embodiment.

Referring now to FIG. 11, a diagram of "look-behind" scanning is illustrated. The optical system 110 is positioned orthogonally with respect to point 1100. However, the second deflector 250 within the optical system (illustrated in FIG. 3) deflects the laser beam 230 backward (with respect to the direction of motion of the gantry 120) at a particular deflection angle θ. During "look-behind" scanning, angle θ increases as a function of the velocity of the gantry 120 and the previous location of the beam 230.

Figure 12:
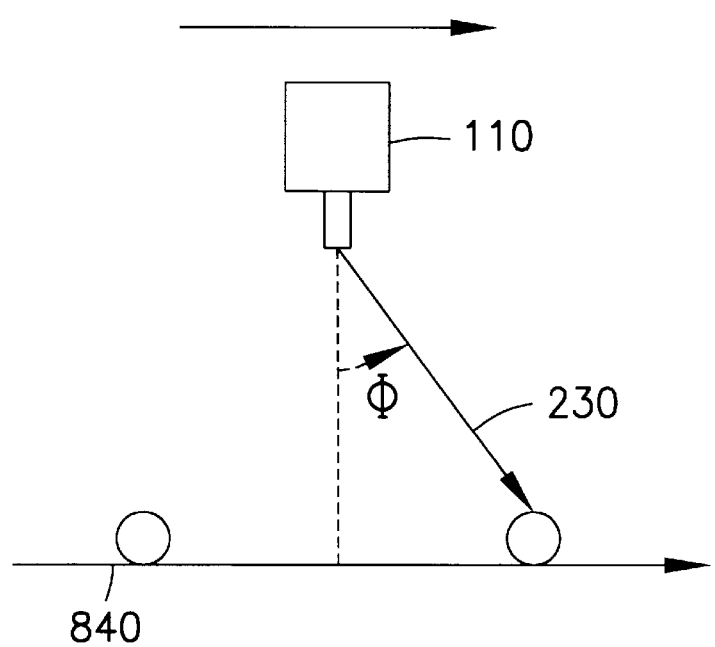
FIG. 12 illustrates "look-ahead" scanning of the exemplary embodiment.

FIG. 12 shows "look-ahead" scanning. Here, while the second deflector 250 deflects the laser beam ahead of the gantry 120 at a particular angle φ. During "look-ahead" scanning, angle φ decreases as a function of the velocity of the gantry 120 and the previous location of the beam 230.

Figure 13:
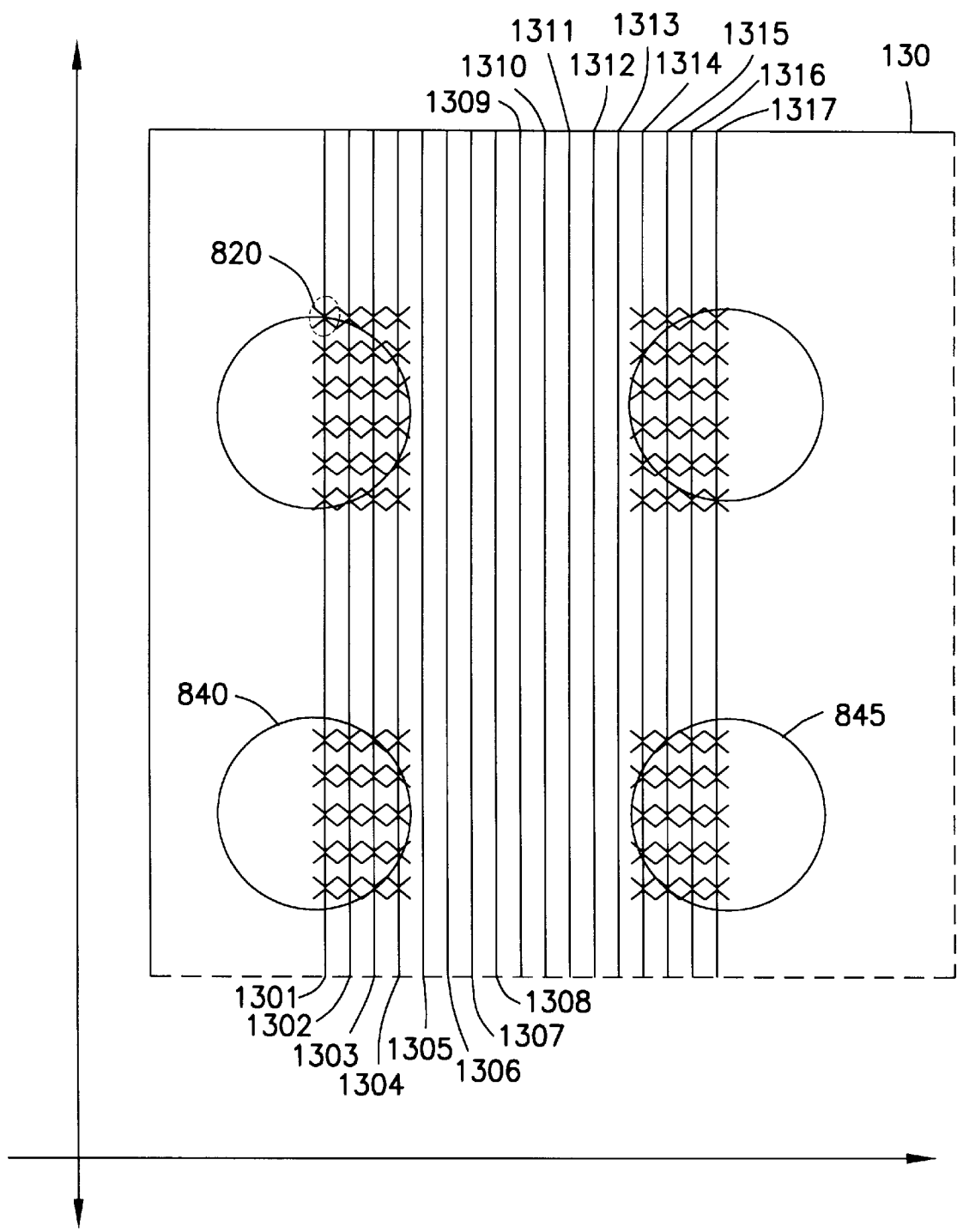
FIG. 13 illustrates one possible application of "look-ahead/look-behind" scanning.

One possible application of "look-ahead/look-behind" scanning is illustrated in FIG. 13. In this example, the velocity of the gantry 120 has been set based on the velocity at which the photo sensitive devices 290, 295 (and process electronics 140 and computer 150) can detect and process reflected light. In particular, the velocity of the gantry 120 is set such that when the optical system 110 is positioned mid-way between two features of interest (along the X-axis), here solder balls 840, the scanning system 110 has scanned one-half of a solder ball. In this example, the gantry moves along the X axis a distance of two scan lines in the time it takes the optical system 110 to collect data points 840 along one scan line.

Assume that gantry 120 positions the optical system 110 directly above line 1301. The light source 240 pulses a light beam 230 along line 1301 at the spots on BGA 130 corresponding to the data points 820 (i.e., in accordance with the technique discussed above in connection with FIG. 10) by the first deflector 240. When the optical system 110 has completed scanning the appropriate points on line 1301 and the first deflector is reset to begin scanning line 1302, the gantry 120 (having moved at a constant velocity) is positioned directly above line 1303. Since the optical system is not orthogonal to the next set of target points (i.e., along line 1302), the second deflector 250 must deflect the laser beam 230 backward (with respect to the motion of the gantry 12) to compensate for the change in angular direction. Accordingly, the process electronics 150 applies a first control voltage to the deflector 250 so that the optical system can scan along line 1302. In this embodiment, the first control voltage is proportional to the necessary deflection angle θ (see FIG. 11).

When the optical system 110 completes scanning the points along line 1302, the gantry 120 is positioned above line 1305, thus a second control voltage—greater in magnitude than the first control voltage (since the required deflection angle θ is greater)—must be applied to the second deflector 250 to compensate for the next change in angular direction to the next scan line, i.e., line 1302. This process continues until half of the solder ball 840 has been scanned, and the gantry 120 has positioned the optical system 120 to directly above line 1308.

The optical system 120 next begins performing "look-ahead" scanning. A control voltage is applied to the second deflector 250 so that the laser beam 230 is deflected to impinge a point ahead of the gantry 120 (relative to the direction of motion of the gantry 120). In the example of FIG. 13, points along line 1317 are scanned. At the time that the optical system 110 completes scanning points along line 1317, the gantry is positioned at line 1310. A second control voltage is applied to the second deflector 250 to compensate for the change in angular direction to the next scan line, i.e., line 1316. In this embodiment, the second control voltage is smaller in magnitude that the first look-ahead control voltage since the optical system is now closer to the target points. This process continues until the first half of the solder ball 845 has been scanned, at which time the optical system is positioned above line 1317. The optical system then begins look-behind scanning again.

Figure 14:
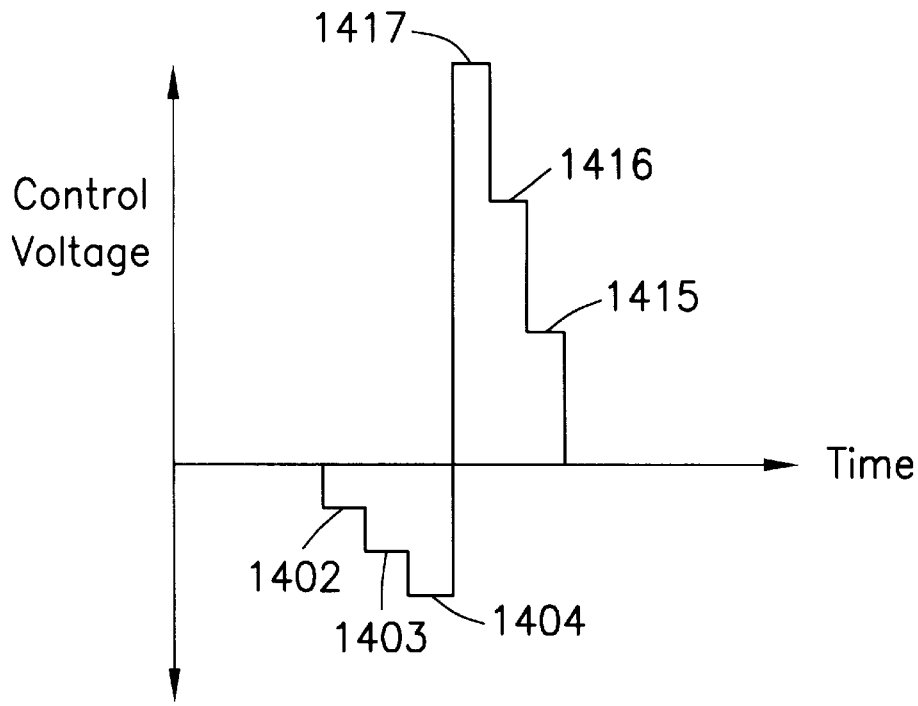
FIG. 14 illustrates a stepped control voltage waveform applied to the second deflector for the "look-ahead/look-behind" scanning.

FIG. 14 illustrates the stepped control voltage waveform applied to the second deflector 250 in this embodiment for the "look-ahead/look-behind" scanning. Each step corresponds to a different scan line. In this example, step 1402 corresponds to scan line 1302, step 1403 corresponds to scan line 1303, etc.

Figure 15:
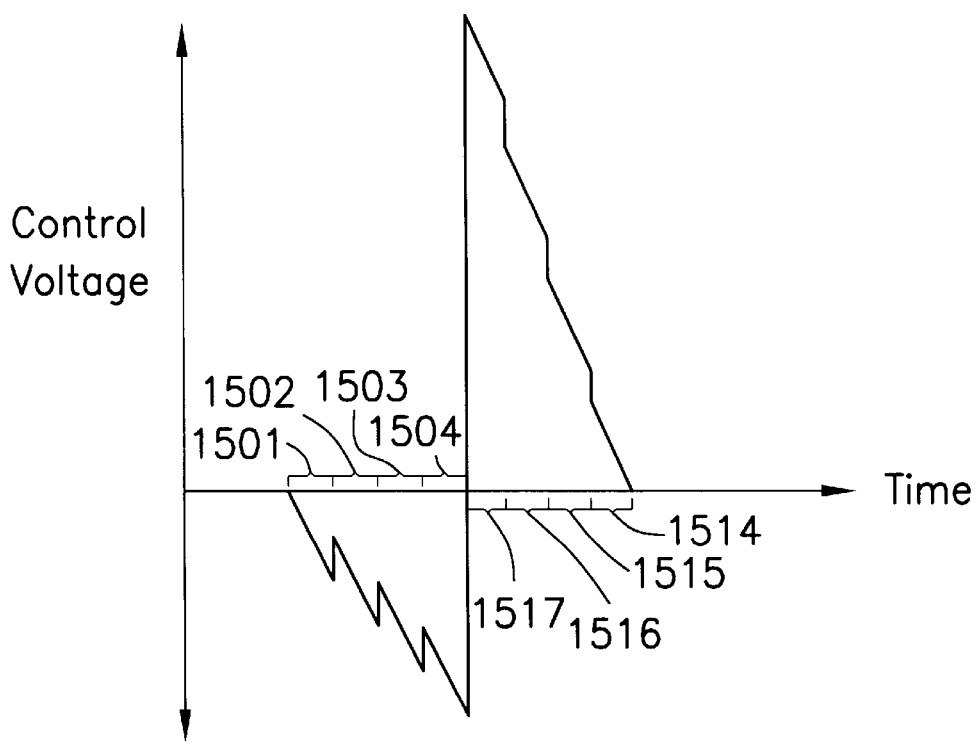
FIG. 15 illustrates an exemplary wave form applied to the second deflector for "look-ahead/look-behind" scanning with full correction

In addition to "look-ahead/look-behind" scanning, the system described in connection with FIG. 13 may also correct the scan lines as described above in connection with FIGS. 4–6. That is, the illustrative system also applies to the second deflector 250 the correction control wave form illustrated in FIG. 5 during "look-behind" scanning, and the correction control wave form illustrated in FIG. 7 during "look-ahead" scanning. As a result, all of the scan lines are orthogonal to the direction of motion of the gantry 120, i.e., each one of scan lines 1301–1304, 1314–1317 is parallel to the Y axis. FIG. 15 illustrates an exemplary wave form applied to the second deflector 250 for "look-ahead/look-behind" scanning with full correction.

Other Alternative Embodiments

While the present invention has been particularly shown and described with reference to exemplary embodiments thereof, it will be understood by those skilled in the art that various changes in form and details may be made therein without departing from the spirit and scope of the invention.

What is claimed is:

1. A method for scanning an object, comprising the steps of:

moving one of a light source and the object in a first direction at a preselected velocity;

emitting a light beam from the light source;

sweeping the light beam in a second direction, the second direction being substantially orthogonal to the first direction;

deflecting the light beam in a third direction at a deflection angle;

focussing the light beam on the object; and changing the deflection angle at a determined rate, the determined rate being determined as a function of the preselected velocity, the focussed light beam scanning the object at a plurality of X-Y coordinates along an axis substantially orthogonal to the first direction.

2. The method of claim 1, wherein the third direction is in a direction substantially opposite to the first direction.

3. The method of claim 1, wherein the third direction is in a direction substantially in the first direction.

4. The method of claim 1, wherein the sweeping step is performed simultaneously with the moving step.

5. The method of claim 4, wherein the deflecting step is performed simultaneously with the moving step.

6. The method of claim 1, further comprising the step of:

detecting at least some light reflected by the object at at least some of the plurality of respective X-Y coordinates.

7. The method of claim 6, wherein the detecting step is performed as a function of a position of a preselected feature on the object.

8. The method according to claim 6, further comprising the step of:

determining a Z coordinate for each of the at least one X-Y coordinate location as a function of the detection step.

9. The method of claim 1, wherein the light beam is focussed on the object only at preselected X-Y coordinates as a function of the position of a preselected feature on the object.

10. The method of claim 1, wherein the changing step includes the step of:

linearly changing the magnitude of the first deflection angle at the first rate.

11. The method of claim 10, wherein the step of linearly changing includes the step of:

linearly increasing the magnitude of the first deflection angle at the first rate.

12. The method of claim 10, wherein the step of linearly changing includes the step of:

linearly decreasing the magnitude of the first deflection angle at the first rate.

13. The method of claim 10, wherein the step of linearly changing includes the steps of:

linearly increasing the magnitude of the first deflection angle at the first rate for a first time period; and linearly decreasing the magnitude of the first deflection angle at the first rate for a second time period.

14. The method of claim 10, further comprising the step of:

resetting the deflection angle to a reset angle after a predetermined interval of time.

15. The method of claim 1, wherein the emitting step includes the step of:

pulsing the light from the light source.

16. The method of claim 1, wherein the focussed light beam scans the object along the axis only if the axis intersects at least one preselected feature of the object.

17. A system for scanning an object, comprising:

a motion mechanism;

a light source for emitting a light beam, the motion mechanism moving one of the light source and the object at a pre-selected velocity in a first direction;

a first deflector for sweeping the light beam in a second direction, the second direction being substantially orthogonal to the first direction;

a second deflector for deflecting the light beam in a third direction at a deflection angle;

a processor controlling the second deflector, the processor changing the deflection angle at a determined rate, the determined rate determined as a function of the preselected velocity; and at least one lens for focussing the light beam on the object, wherein the focussed light beam scans the object at a plurality of X-Y coordinates along an axis substantially orthogonal to the first direction.

18. The system of claim 17, wherein the first deflector includes an acousto-optic deflector.

19. The system of claim 18, wherein the second deflector includes an acousto-optic deflector.

20. The system of claim 17, further comprising:

at least one photo-sensitive detector for detecting light deflected from the object at at least some of the plurality of X-Y coordinates and for generating a respective signal as a function of the detected light reflected from the object at each of the at least some of the plurality of X-Y coordinates.

21. The system of claim 20, wherein the at least one photo-sensitive detector generates each respective signal as a function of a position that the deflected light impinged the photo-sensitive detector.

22. The system of claim 20, further comprising:

process electronics for processing each respective signal from the at least one photo-sensitive detector.

23. The system of claim 17, further comprising:

at least one photo-sensitive detector for detecting light reflected from the object at a plurality of X-Y coordinates as a function of a position of a feature on the object.

24. The system of claim of claim 17, wherein the focussed light beam scans the object along the axis only if the axis intersects at least one preselected feature of the object.

25. A method for scanning an object, comprising the steps of:

moving one of a light source and the object in a first direction at a preselected velocity;

emitting a light beam from the light source;

sweeping the light beam in a second direction, the second direction being substantially orthogonal to the first direction;

deflecting the light beam in a third direction at a deflection angle;

focussing the light beam on the object at a plurality of X-Y coordinates;

increasing the deflection angle at a determined rate for a first predetermined time period, the determined rate being determined as a function of the preselected velocity; and decreasing the deflection angle at the determined rate for a second predetermined time period.

26. The method of claim 25, wherein the increasing step includes the step of linearly increasing the deflection angle at the determined rate.

27. The method of claim 26, wherein the decreasing step includes the step of linearly decreasing the deflection angle at the determined rate.

28. The method of claim 25, further comprising the step of:

detecting at least some light reflected by the object at at least some of the plurality of respective X-Y coordinates.

29. The method of claim 28, wherein the detecting step is performed as a function of a position of a preselected feature on the object.

30. The method according to claim 28, further comprising the step of:

determining a Z coordinate for each of the plurality of respective X-Y coordinates as a function of the detecting step.

31. The method of claim 25, wherein the light beam is focussed on the object only at preselected X-Y coordinates as a function of the position of a preselected feature on the object.

32. The method of claim 25, further comprising the step of:

resetting the deflection angle to a reset angle after a predetermined interval of time.

33. The method of claim 25, wherein the emitting step includes the step of:

pulsing the light from the light source.

34. The method of claim 25, wherein the focussed light beam scans the object along an axis that is substantially orthogonal to the first direction.

35. The method of claim 25, wherein the focussed light beam scans the object along the axis only if the axis intersects at least one preselected feature on the object.

36. The method of claim 25, further comprising the steps of:

increasing the preselected velocity for a predetermined time after an object feature is scanned.

37. A system for scanning an object, comprising:

a motion mechanism;

a light source for emitting a light beam, the motion mechanism moving one of the light source and the object at a pre-selected velocity in a first direction;

a first deflector for sweeping the light beam in a second direction, the second direction being substantially orthogonal to the first direction;

a second deflector for deflecting the light beam in a third direction at a deflection angle;

a processor controlling the second deflector, the processor increasing the deflection angle at a determined rate for a first time period, the determined rate determined as a function of the preselected velocity, the processor further decreasing the deflection angle at the determined rate for a second time period; and at least one lens for focusing the light beam on the object.

38. The system of claim 37, wherein the processor linearly increases the deflection angle at the determined rate.

39. The system of claim 38, wherein the processor linearly decreases the deflection angle at the determined rate.

40. The system of claim 37, wherein the first deflector includes an acousto-optic deflector.

41. The system of claim 40, wherein the second deflector includes an acousto-optic deflector.

42. The system of claim 37, further comprising:

at least one photo-sensitive detector for detecting light deflected from the object at a plurality of X-Y coordinates and for generating a respective signal as a function of the detected light reflected from the object at each of the plurality of X-Y coordinates.

43. The system of claim 42, wherein the at least one photo-sensitive detector generates each respective signal as a function of a position that the deflected light impinged the photo-sensitive detector.

44. The system of claim 43, further comprising:

process electronics for processing each respective signal from the at least one photo-sensitive detector.

45. The system of claim 37, further comprising:

at least one photo-sensitive detector for detecting light reflected from the object at a plurality of X-Y coordinates as a function of a position of a feature on the object.

46. The system of claim of claim 37, wherein the focussed light beam scans the object along an axis substantially orthogonal to the first direction.

47. The system of claim 37, wherein the focussed light beam scans the object along the axis only if the axis intersects at least one preselected feature of the object.

48. A method for scanning an object, comprising the steps of:

moving one of a light source and the object in a first direction at a preselected velocity;

emitting a light beam from the light source;

simultaneous to the moving step, sweeping the light beam in a second direction, the second direction being substantially orthogonal to the first direction, wherein the light beam is swept at a first velocity during a first predetermined time period, and is swept at a second velocity during a second predetermined time period; and focusing the swept light beam on the object at a plurality of X-Y coordinates.

49. The method of claim 48, wherein the first determined time period and the second determined time period are determined as a function of a position of a feature on the object.

50. The method of claim 48, wherein the emitting step is performed during the first predetermined time period and the emitting step is not performed during the second predetermined time period, and wherein a first magnitude of the first velocity is less than a second magnitude of the second velocity.

51. The method of claim 50, wherein the light beam scans a preselected feature of the object during the first time period.

52. The method of claim 48, further comprising the step of detecting light reflected from the object at a subset of the plurality of X-Y coordinates.

\* \* \* \* \*